US00PP23494P2

(12) United States Plant Patent
Lintott et al.

(10) Patent No.: US PP23,494 P2
(45) Date of Patent: Mar. 19, 2013

(54) ***GAILLARDIA* PLANT NAMED 'FANFARE BLAZE'**

(50) Latin Name: *Gaillardia×grandiflora*
Varietal Denomination: FANFARE BLAZE

(76) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 98 days.

(21) Appl. No.: 12/932,494

(22) Filed: Feb. 24, 2011

(51) Int. Cl.
*A01H 5/00* (2006.01)

(52) U.S. Cl. ..... Plt./431

(58) Field of Classification Search ..... Plt./431
See application file for complete search history.

*Primary Examiner* — June Hwu

(57) ABSTRACT

A new cultivar of *Gaillardia* named 'FANFARE BLAZE' that is distinguishable by a long blooming period, gray-green leaves, a compact, low-growing habit and large inflorescences composed of brilliant orange-red tubular ray flowers with yellow apices. In combination these traits set 'FANFARE BLAZE' apart from all other existing varieties of *Gaillardia* known to the inventors.

3 Drawing Sheets

Genus: *GAILLARDIA*.
Species: *×grandiflora*.
Denomination: 'FANFARE BLAZE'.

BACKGROUND OF THE INVENTION

The present invention relates to a new and distinct cultivar of blanket flower, an herbaceous perennial that is grown for use as an ornamental landscape and container plant. The new invention is known botanically as *Gaillardia×grandiflora* and will be referred to hereinafter by the cultivar name 'FANFARE BLAZE'. *Gaillardia* is in the family Compositae, under which the commonly referred to "flower" is actually the inflorescence, and made up of smaller ray flowers and disc florets. The ray flowers themselves have the appearance of "petals".

'FANFARE BLAZE' is product of a *Gaillardia* breeding program started by the inventors in 2006. The breeding program is conducted in a greenhouse in a nursery environment in West Sussex, United Kingdom. The aims of the breeding program are to produce novel combinations of flower colors and flower forms which are borne on well-branched plants with sturdy growth habits. The inventors selected 'FANFARE BLAZE' in 2007 for its bright orange-red flowers which are produced continually from spring until fall and which do not fade with age. The inventors also selected for its compact and naturally branching habit.

'FANFARE BLAZE' resulted from the controlled cross pollination as follows: The female parent of 'FANFARE BLAZE' is *Gaillardia* 'Fanfare' (U.S. Plant Pat. No. 15,892) which was discovered as a chance seedling by one of the inventors in 1997. The male parent of 'FANFARE BLAZE' is an unreleased and unpatented seedling of the inventors' origin, code number G5.

'FANFARE BLAZE' is distinguishable from the female parent as follows: Whereas the female parent exhibits yellow and red tubular bi-colored flowers, the flowers of 'FANFARE BLAZE' are also tubular but orange-red in color and less notably bi-colored. 'FANFARE BLAZE' also grows with a more compact and freely-branching habit than the female parent. Finally, 'FANFARE BLAZE' remains in flower longer, until late fall.

'FANFARE BLAZE' is distinguishable from the male parent as follows: Whereas the male parent exhibits flat petals, the petals of 'FANFARE BLAZE' are tubular.

The variety of *Gaillardia* which is considered by the inventors to most closely resemble 'FANFARE BLAZE' is the female parent variety, 'Fanfare'. The two varieties are compared above. The inventors consider that the variety of *Gaillardia* plant known as 'Tizzy' (U.S. Plant Pat. No. 19,944) is similar to 'FANFARE BLAZE' in respect of its tubular ray flowers. However, the tubular ray flowers of 'Tizzy' are red in color whereas the tubular ray flowers of 'FANFARE BLAZE' are orange-red in color and exhibit a prominent bright petal apex when the inflorescence is fully expanded.

Asexual reproduction of the new cultivar 'FANFARE BLAZE' was first accomplished by the inventors in 2007. The method of asexual propagation used was vegetative cuttings taken from the original selection which was growing in an unheated greenhouse in West Sussex, United Kingdom. Subsequent asexual propagations have been carried out by the inventors in the same greenhouse using both vegetative cuttings and root cuttings. The inventors have determined that 'FANFARE BLAZE' is stable and reproduces true to type in successive generations of asexual reproduction by either method.

SUMMARY OF THE INVENTION

The following traits have been repeatedly observed and represent the distinguishing characteristics of 'FANFARE BLAZE'. These traits in combination distinguish 'FANFARE BLAZE' from all other existing varieties of *Gaillardia×grandiflora* known to the inventors. 'FANFARE BLAZE' has not been tested under all possible conditions and phenotypic differences may be observed with variations in environmental, climatic, and cultural conditions, however, without any variance in genotype.

1. 'FANFARE BLAZE' exhibits a compact and naturally branching plant habit.

2. 'FANFARE BLAZE' exhibits large inflorescences composed of numerous bright orange-red tubular ray flowers.
3. The petals of the tubular ray flowers of 'FANFARE BLAZE' are entirely scarlet in color when the inflorescence is newly open.
4. As the inflorescence expands, the petals of the tubular ray flowers develop an orange-red color. At the same time, the petal apex develops a yellow coloration which becomes prominent when the inflorescence is fully expanded.
5. The disc flowers of 'FANFARE BLAZE' are yellow when the inflorescence is newly opening, becoming crimson when the inflorescence is fully expanded.
6. 'FANFARE BLAZE' blooms continually from spring until late fall.
7. After one year's growth in a 3 liter container, 'FANFARE BLAZE' is 35 cm-40 cm in height and 40 cm-45 cm in width.
8. At maturity in the ground, 'FANFARE BLAZE' is 40 cm-45 cm in height and 50 cm-55 cm in width.
9. 'FANFARE BLAZE' is hardy to USDA Zone 5.

BRIEF DESCRIPTION OF THE DRAWINGS

The accompanying color drawings illustrate the overall appearance of the new *Gaillardia* cultivar 'FANFARE BLAZE' showing the colors as true as is reasonably possible to obtain in colored reproductions of this type. Colors in the photographs may differ from the color values cited in the detailed botanical description, which more accurately describes the actual colors of the new variety 'FANFARE BLAZE'.

The drawing labeled as FIG. 1 depicts a whole plant of 'FANFARE BLAZE' which has been grown in a frost-free greenhouse in West Sussex, United Kingdom. The illustrated plant is one year old and has been grown without any pinching or chemical growth regulator.

Figure 1:
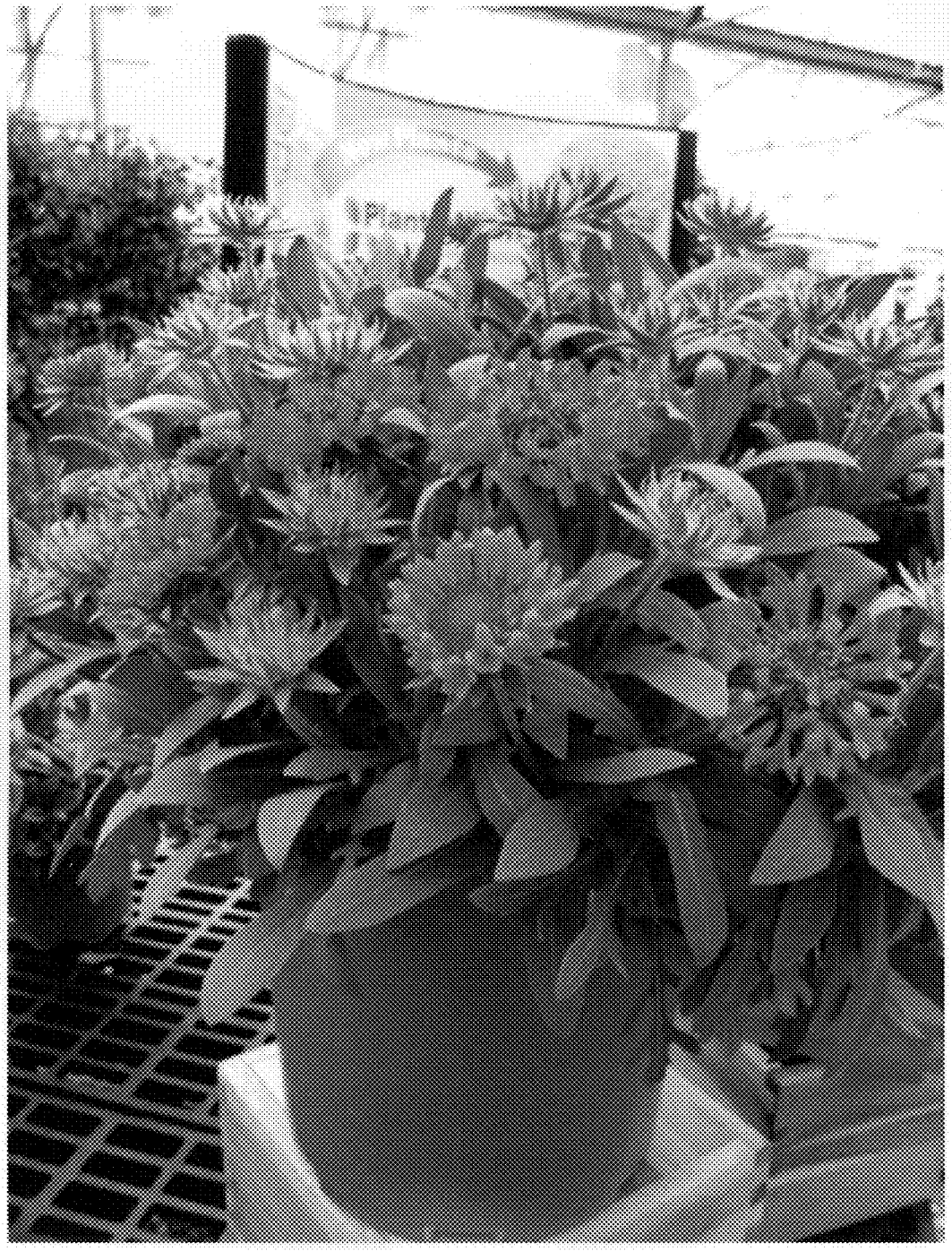
Figure 2:
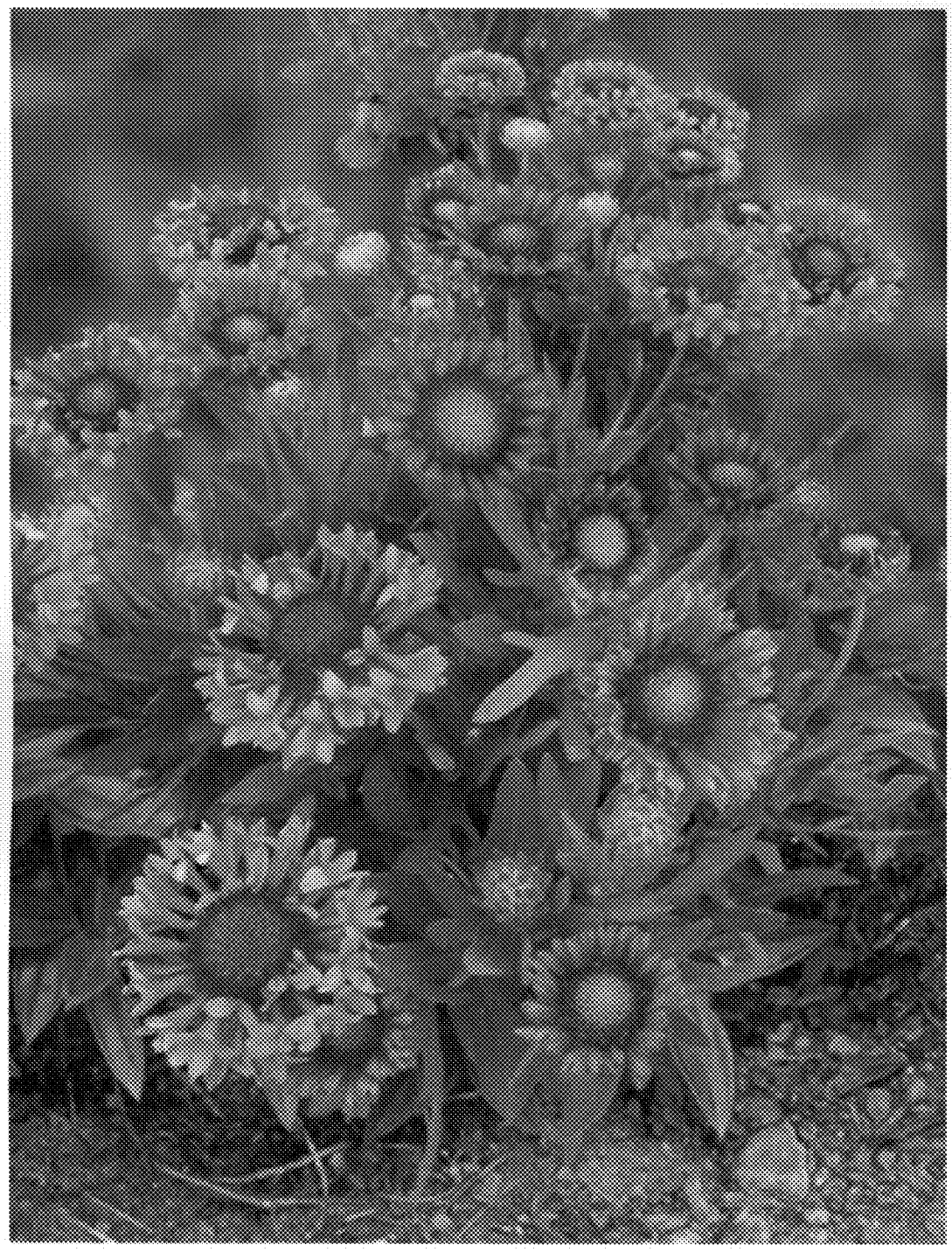

The drawing labeled as FIG. 2 depicts a whole plant of 'FANFARE BLAZE' viewed from above and grown under the same conditions as the plant in FIG. 1. This drawing illustrates the inflorescence at all stages from bud to newly-opened to fully-opened to senescent.

Figure 3:
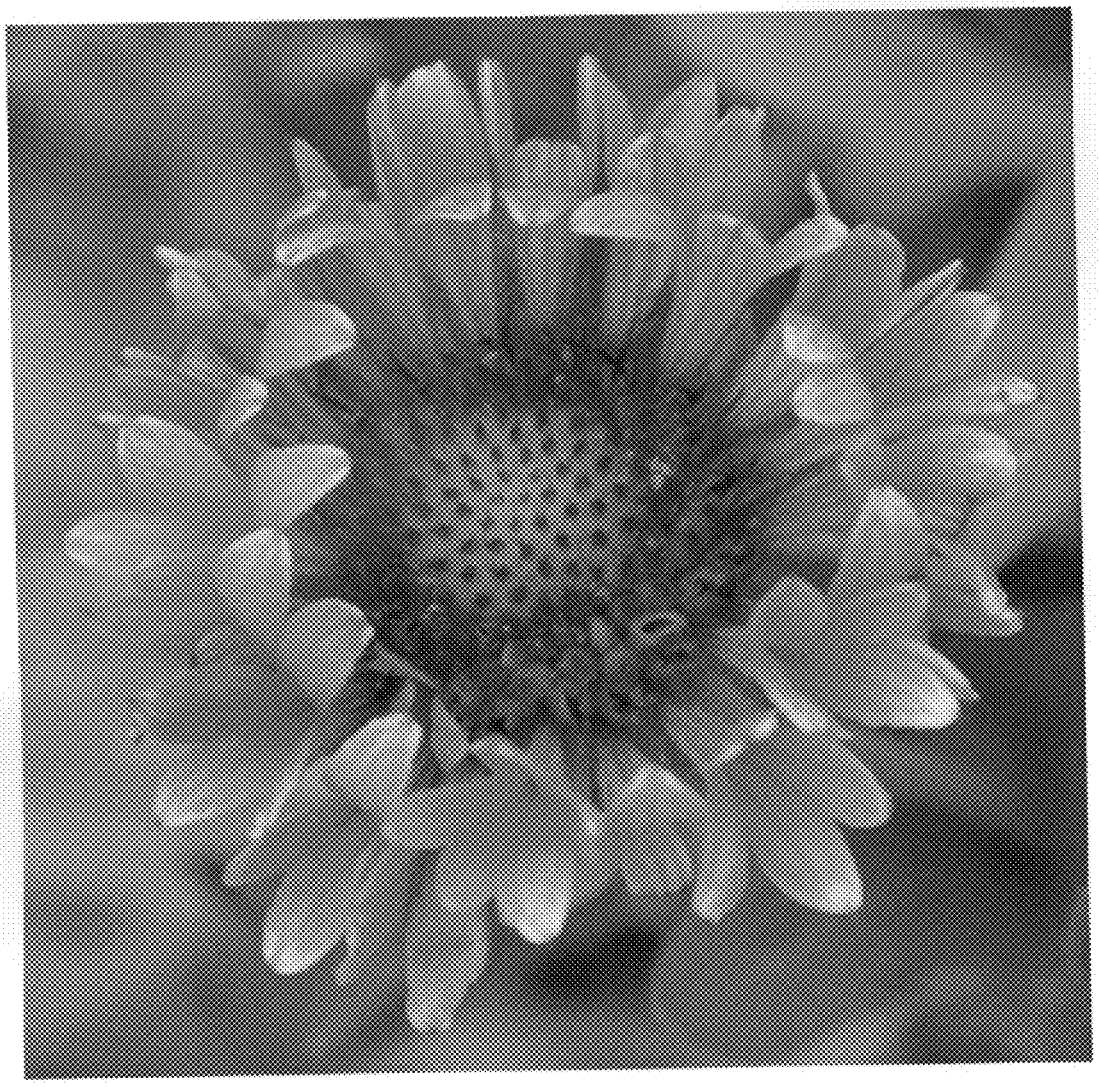

The drawing labeled as FIG. 3 depicts a close up view of the fully expanded inflorescence of 'FANFARE BLAZE'.

BOTANICAL DESCRIPTION OF THE PLANT

The following is a detailed botanical description of the new *Gaillardia×grandiflora* cultivar 'FANFARE BLAZE'. Observations, measurements, values and comparisons were compiled in Santa Barbara, Calif. from a one year old plant growing out of doors in full sun in freely drained garden loam. Color determinations are made in accordance with the 2007 edition of The Royal Horticultural Society Colour Chart from London England, except where general color terms of ordinary dictionary significance are used.

Botanical classification: *Gaillardia×grandiflora.*

Genus: *Gaillardia.*

Species: *×grandiflora.*

Common name: Blanket flower.

Parentage: *Gaillardia×grandiflora* 'FANFARE BLAZE' resulted from the controlled cross pollination between:

*Female parent.*—*Gaillardia* 'Fanfare' (U.S. Plant Pat. No. 15,892).

*Male parent.*—An unreleased and unpatented seedling of the inventors' origin, code number G5.

Propagation method: Typically by softwood cuttings although root cuttings have also been successful.

Rooting system: Fine and fibrous.

Vigor: Moderate vigor.

Time to develop roots: 14 to 20 days are needed for an initial cutting to develop roots.

Temperature to develop roots: The recommended air temperature is 20-21° Centigrade.

Crop time: Approximately 10 weeks to 2 months are needed to produce a 15-centimeter container from a rooted cutting.

Growth habit: Compact and naturally freely branching.

Suggested container size: 15-centimeter container.

Use: Ornamental for use as a landscape plant or container plant.

Type: Herbaceous perennial.

Overall dimensions: After one year's growth in a 3 liter container: 35-40 cm in height and 40 cm-45 cm in width.

*At maturity in the ground.*—40-45 cm in height and 50-55 cm in width.

Cultural requirements: Grow in full sun with moderate water, and well-draining soil such as loam.

Resistance to pests and diseases: 'FANFARE BLAZE' has not been observed to exhibit any resistance to any particular pest or disease. 'FANFARE BLAZE' is susceptible to downy mildew and to thrips as may be typical of *Gaillardia.*

Hardiness: USDA Zone 5.

Growing requirements: If grown outside in regions which experience winter freezing, 'FANFARE BLAZE' may be started as a cutting during the spring or summer of the previous year, planted out prior to the onset of winter, and flowering will commence typically in May or June according to the region and season. When grown outside in frost-free regions, or in frost-protected greenhouses, 'FANFARE BLAZE' will flower virtually all year round and may be started as a cutting (which should be non-flowering) at any time of year.

Stem:

*Branching habit.*—Basal branching.

*Stem color* (*juvenile growth*).—138D.

*Stem color* (*stem is mature*).—184B.

*Stem dimensions.*—9-12 cm in length and 5 mm. in width.

*Stem shape.*—Cylindrical, slightly fluted longitudinally.

*Stem surface.*—Markedly villous with dense coverage of very fine silvery hairs, approximately 3 mm in length.

*Internode length.*—Average internode length is 15-18 mm.

Foliage:

*Type.*—Evergreen.

*Leaf arrangement.*—Alternate.

*Leaf form.*—Predominantly linear with occasional pair of protruding lobes and (rarely) multiple opposite lobes as in an oak leaf.

*Margin.*—Entire.

*Leaf shape.*—Linear.

*Leaf length.*—10 cm.

*Leaf width.*—2 cm.

*Lobes* (*where present as one pair*).—2 cm in length, 0.75 cm in width, shape linear, apex rounded.

*Lobes* (*where present in multiple pairs*).—4 cm in length, 0.75 cm in width, shape linear, apex rounded.

*Leaf base*.—Attenuate.
*Leaf apex*.—Rounded.
*Leaf attachment*.—Sessile.
*Leaf color* (*both surfaces*).—138A.
*Leaf venation pattern*.—Parallel. Mid vein protrudes on both surfaces.
*Vein color* (*both surfaces*).—138B.
*Leaf surface* (*both surfaces*).—Pubescent, very fine silvery hairs, lighter than 202D; approximately 3 mm in length.
*Fragrance*.—A slight sage-like scent when bruised.

Inflorescence:
*Inflorescence*.—Solitary.
*Aspect*.—Facing upward.
*Dimensions of inflorescence*.—65-70 mm in diameter and 25 mm in height.
*Inflorescence type*.—Radiate capitate.
*Inflorescence shape*.—Radiate with center disc.
*Disc diameter* (*inflorescence fully expanded*).—30 mm.
*Inflorescence number per plant*.—Very numerous: a mature one-year old plant bears approximately 100 inflorescences in bud and flower at one time.
*Blooming season*.—Spring, summer and fall.
*Lastingness of inflorescence*.—10 days, reducing to 7 days in full sun in mid-summer.
*Peduncle dimensions*.—7-9 cm in length and 3 mm in width.
*Peduncle shape*.—Cylindrical.
*Peduncle surface*.—Surface is pubescent and exhibits longitudinal ridges.
*Peduncle color*.—138D.
*Peduncle strength*.—Moderate.
*Immature inflorescence shape* (*bud*).—Closest to rotate whorl.
*Immature inflorescence dimensions* (*bud*).—3 cm in diameter and 1.50 cm in length.
*Color of immature inflorescence* (*bud*).—138B.
*Surface of immature inflorescence* (*bud*).—Villous.
*Ray flower shape*.—Tubular.
*Ray flower surface* (*outer surface*).—Pubescent.
*Ray flower surface* (*inner surface*).—Glabrous.
*Ray flower arrangement*.—Radiate.
*Number of ray flowers per inflorescence*.—25 to 35 ray flowers per inflorescence.
*Number of petals per ray flower*.—Four.
*Fused or unfused*.—Petals are basally fused.
*Petal margins of ray flowers*.—Entire.
*Ray flower dimensions*.—3.0 cm in length including the corolla tube, 1.0 cm in width at the apex.
*Corolla tube dimensions*.—15 mm in depth and 5 mm in diameter.
*Color of ray flowers* (*inflorescence newly opening, both surfaces*).—N34A.
*Color of ray flowers* (*inflorescence fully expanded, both surfaces*).—Base of tube N34B becoming 32A towards apex; apex 8A.
*Ray flower veins* (*both surfaces*).—Longitudinal, parallel, fine but prominent; color N34A.
*Self-cleaning or persistent*.—Self-cleaning.
*Quantity of disc florets per inflorescence*.—Numerous, approximately 200-250.
*Disc floret dimensions* (*including pistil length*).—9 mm in length and 2.5 mm in width.
*Depth of disc floret corolla tube*.—6 mm in depth.
*Surface of disc florets*.—Lanate.
*Color of disc flowers* (*inflorescence newly opening, both surfaces*).—12A.
*Color of disc flowers* (*inflorescence fully expanded, both surfaces*).—N34A.
*Phyllary dimensions*.—5.50 cm in diameter and 3 cm in length.
*Phyllary color*.—147B.
*Phyllary arrangement*.—Whorl.
*Number of involucral bracts*.—An average of 25 in number per inflorescence.
*Shape of involucral bract*.—Oblanceolate.
*Involucral bract dimensions*.—2 cm in length and 0.50 cm in width.
*Involucral bract margin*.—Entire.
*Involucral bract apex*.—Acute.
*Involucral bract base*.—Truncate.
*Involucral bract color* (*both surfaces*).—138B.
*Involucral bract surface* (*abaxial surface*).—Pubescent.
*Involucral bract surface* (*adaxial surface*).—Pubescent.
*Fragrance of inflorescence*.—Sweet fragrance.

Reproductive organs:
*Stamens* (*present on disc florets only*).—Three in number, adnate to inner surface of corolla tube.
*Stamen dimensions*.—0.20 mm in width and 5 mm in length.
*Stamen color*.—17A.
*Stamen form*.—Plumose.
*Anther dimensions*.—0.50 mm in length and 1 mm in width.
*Anther color*.—187A.
*Anther shape*.—Narrow lanceolate.
*Pollen*.—Present.
*Quantity of pollen*.—Large amount.
*Pollen color*.—17C.
*Pistil* (*present on ray florets and disc florets*).—One per floret.
*Pistil length*.—12 mm in length.
*Style dimensions*.—2 mm in length and 1 mm in width.
*Style color*.—150D.
*Stigma dimensions*.—8 mm in length and 1.75 mm in width.
*Stigma form*.—Plumose.
*Stigma color*.—187A.
*Stigma shape*.—Bifurcate.
*Ovary position*.—Inferior.
*Ovary color*.—150D.
*Ovary shape*.—Globose.
*Ovary dimensions*.—1 mm in width and 2 mm in height.

Seed:
*Number of seeds*.—80-90 seeds per inflorescence.
*Seed dimensions*.—1 mm in length and 0.50 mm in width.
*Seed color*.—199D.
*Seed surface*.—Bristled, color: 156A.
*Seed shape*.—Piriform.

The invention claimed is:

1. A new and distinct cultivar of *Gaillardia×grandiflora* plant named 'FANFARE BLAZE' as described and illustrated herein.

* * * * *